(12) United States Patent
Eriksson et al.

(10) Patent No.: US 9,345,687 B2
(45) Date of Patent: May 24, 2016

(54) PHARMACEUTICAL COMPOSITIONS OF ANISOMELIC ACID AND THE USE THEREOF

(71) Applicants: John E. Eriksson, Turku (FI); Preethy Paul, Turku (FI); Emilia Peuhu, Turku (FI); M. A. Akbarsha, Tiruchirappalli (IN)

(72) Inventors: John E. Eriksson, Turku (FI); Preethy Paul, Turku (FI); Emilia Peuhu, Turku (FI); M. A. Akbarsha, Tiruchirappalli (IN)

( * ) Notice: Subject to any disclaimer, the term of this patent is extended or adjusted under 35 U.S.C. 154(b) by 0 days.

(21) Appl. No.: 14/423,711

(22) PCT Filed: Aug. 28, 2013

(86) PCT No.: PCT/FI2013/050828
§ 371 (c)(1),
(2) Date: Feb. 25, 2015

(87) PCT Pub. No.: WO2014/033366
PCT Pub. Date: Mar. 6, 2014

(65) Prior Publication Data
US 2015/0202180 A1   Jul. 23, 2015

(30) Foreign Application Priority Data

Aug. 28, 2012   (FI) ...................................... 20125888

(51) Int. Cl.
| | | |
|---|---|---|
| *A61K 9/66* | (2006.01) | |
| *A61K 38/00* | (2006.01) | |
| *A61K 31/34* | (2006.01) | |
| *C07D 307/00* | (2006.01) | |
| *A61K 31/365* | (2006.01) | |
| *A61K 9/00* | (2006.01) | |
| *A61K 9/107* | (2006.01) | |
| *A61K 9/48* | (2006.01) | |

(52) U.S. Cl.
CPC ............. *A61K 31/365* (2013.01); *A61K 9/0014* (2013.01); *A61K 9/107* (2013.01); *A61K 9/4825* (2013.01)

(58) Field of Classification Search
None
See application file for complete search history.

(56) References Cited

U.S. PATENT DOCUMENTS

2009/0291976 A1   11/2009   Ferchmin et al.

FOREIGN PATENT DOCUMENTS

| TW | 102552389 A | 7/2012 |
|---|---|---|
| TW | 201225970 A1 | 7/2012 |

OTHER PUBLICATIONS

Preethy et al.; J. Pharmacology and Pharmacotherapeutics; Jan.-Mar. 2012; vol. 3, No. 1, pp. 26-34.*
Arisawa M et al: "Biological Active Macrocyclic Diterpenoids from Chinese Drug Fáng Féng Cáo; II. Derivatives of Ovatodiolids and Their Cytotoxicity", Planta Medica, Thieme Verlag, DE, Aug. 1986.
Chang Tsui-Ling et al: "5,6,3',4'-Tetrahydroxy-7-Methoxyflavone as a Novel Potential Proteasome Inhibitor", Planta Medica, Jul. 2010.
Chen Yu-Li et al: "Bioactive Cembrane Diterpenoids of Anisomeles Indica", Journal of Natural Products, American Chemical Society, Jul. 25, 2008.
Gershanik T et al: "Self-Dispersing Lipid Formulations for Improving Oral Absorption of Lipophilic Drugs", European Journal of Pharmaceutics and Biopharmaceutics, Jul. 3, 2000.
Lipke M M: "An Armamentarium of Wart Treatments", Clinical Medicine & Research, Dec. 2006.
Preethy C et al: "Analysis of the Cytotoxic Potential of Anisomelic Acid Isolated from *Anisomeles malabarica*", Scientia Pharmaceutica Jun. 2013, Jun. 2013.
Preethy C et al: "Antiproliferative Property of n-hexane and Chloroform Extracts of *Anisomeles malabarica*(L). R.Br. in HPV16-Positive Human Cervical Cancer Cells", Journal of Pharmacology and Pharmacotherapeutics 2012 Medknow Publications and Media PVT. Jan. 2012.
Wang K L: "Current Trends in Treating Cervical Cancer", International Journal of Gerontology, Jun. 2007.
Hou Yu-Yi et al: "The Natural Diterpenoid Ovatodiolide Induces Cell Cycle Arrest and Apoptosis in Human Oral Squamous Cell Carcinoma Ca9-22 Cells", Life Sciences 85, 2009.
Hsieh Shih-Chuan et al: "Inhibition of Pro-Inflammatory Mediators and Tumor Cell Proliferation by *Anisomeles indica* Extracts", Journal of Ethnopharmacology 118, 2008.
Liao Ya-Fan et al: "Aqueous Extract of *Anisomeles indica* and its Purified Compound Exerts Anti-Metastatic Activity Through Inhibition of NF-jB/AP-1-Dependent MMP-9 Activation in Human Breast Cancer MCF-7 Cells", Food and Chemical Toxicology 50, 2012.

* cited by examiner

*Primary Examiner* — Jeffrey T Palenik
(74) *Attorney, Agent, or Firm* — Seppo Laine Oy

(57) ABSTRACT

A pharmaceutical composition for anti-viral cancer treatment in mammals, comprising a therapeutically effective amount of Anisomelic acid or salts thereof. The pharmaceutical composition may comprise Anisomelic acid or salt thereof in an oil-in-water emulsion, for example in an isotropic mixture of at least one oil and at least one surfactant or, alternatively, in a hydrophilic solvent and a co-solvents or surfactant or a combination thereof. A method of treating or preventing of cancer in a mammal, wherein the p53 pathway is deregulated by viral oncoproteins, is also provided.

22 Claims, 11 Drawing Sheets

A
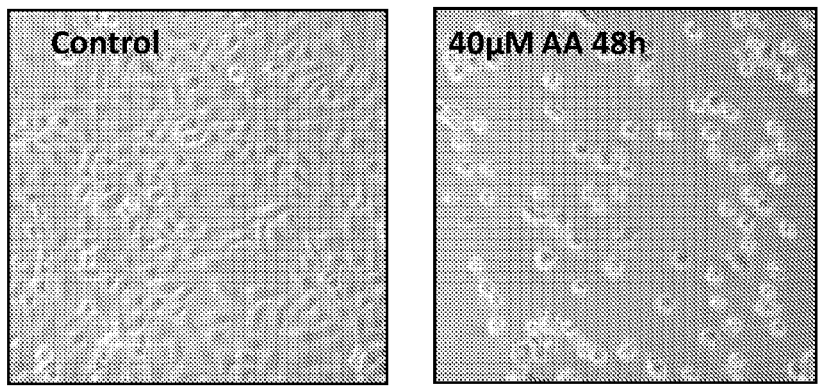
B
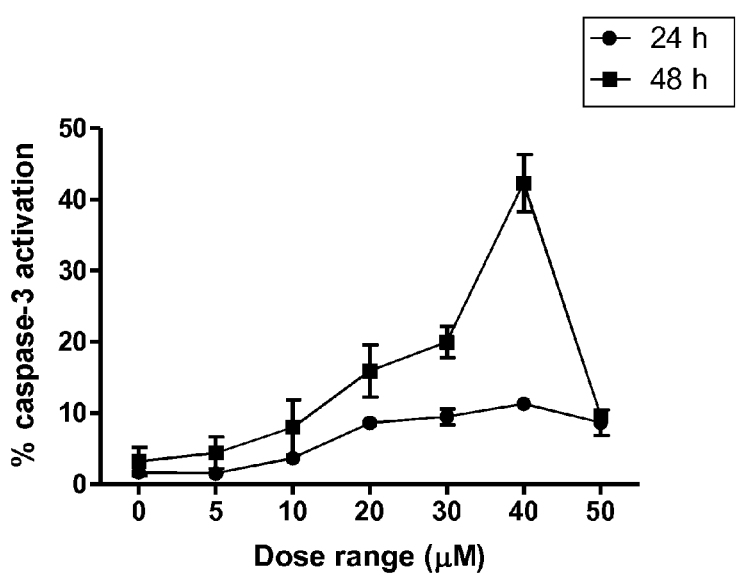
C
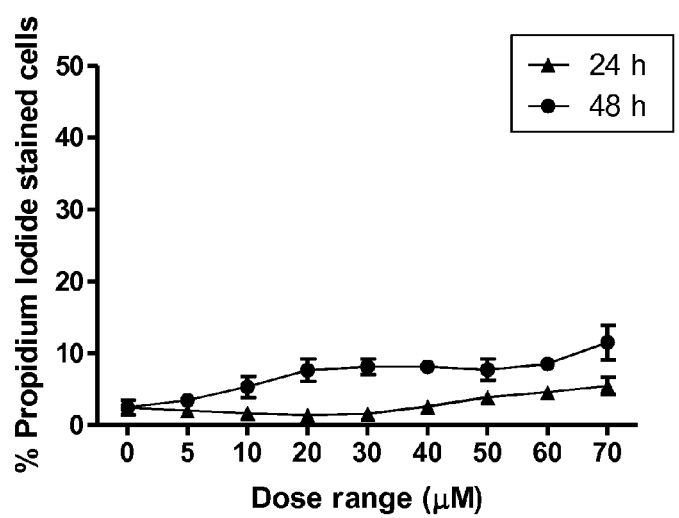
Figs. 1 A- C

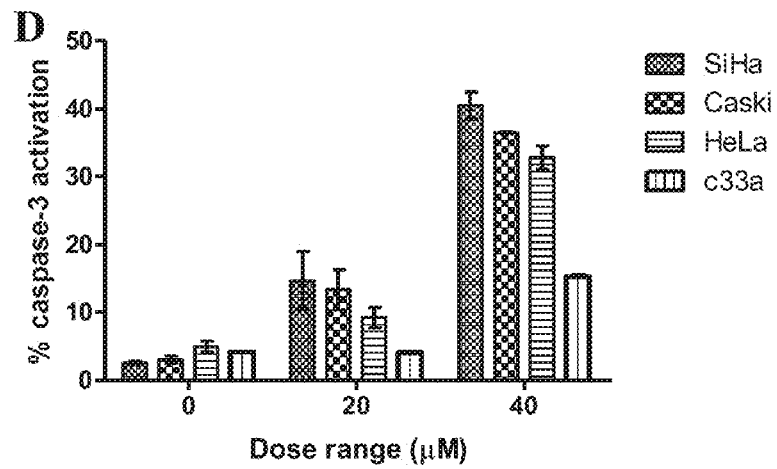
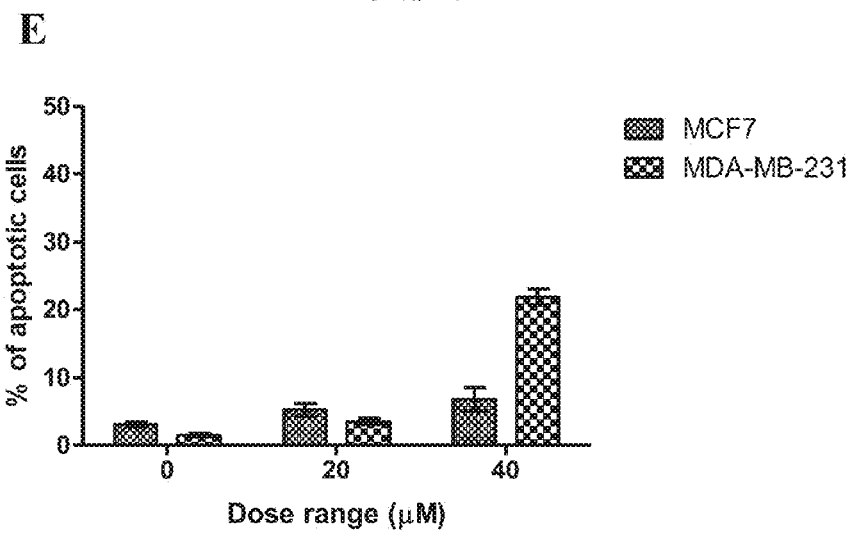
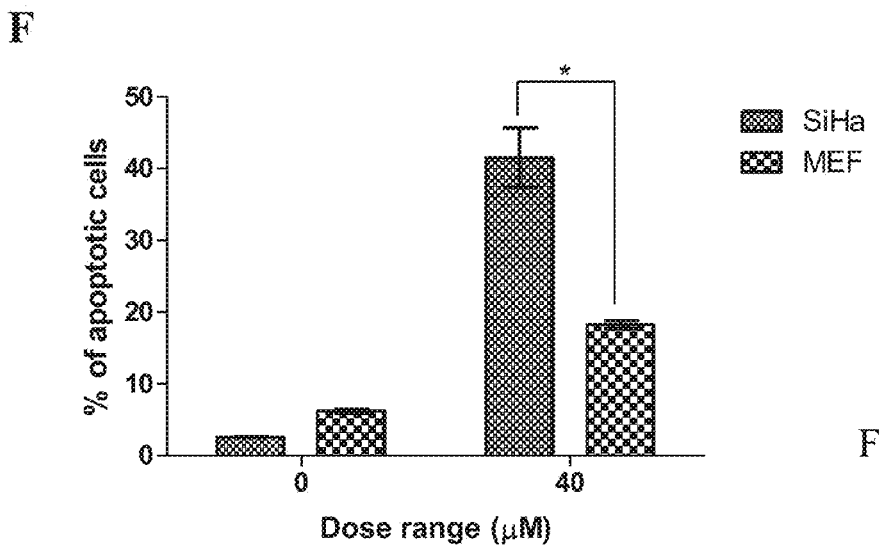
Figs. 1 D-F

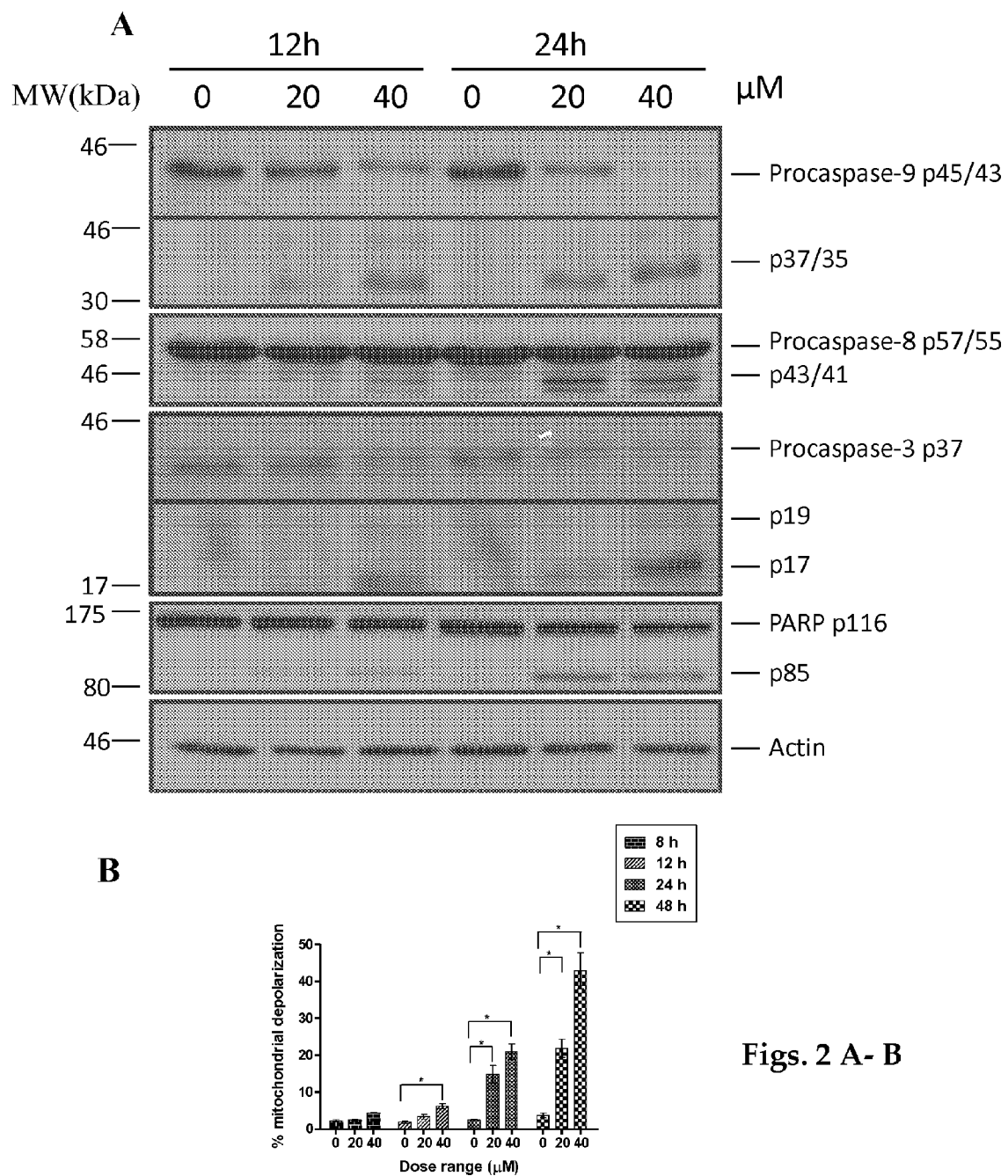
Figs. 2 A-B

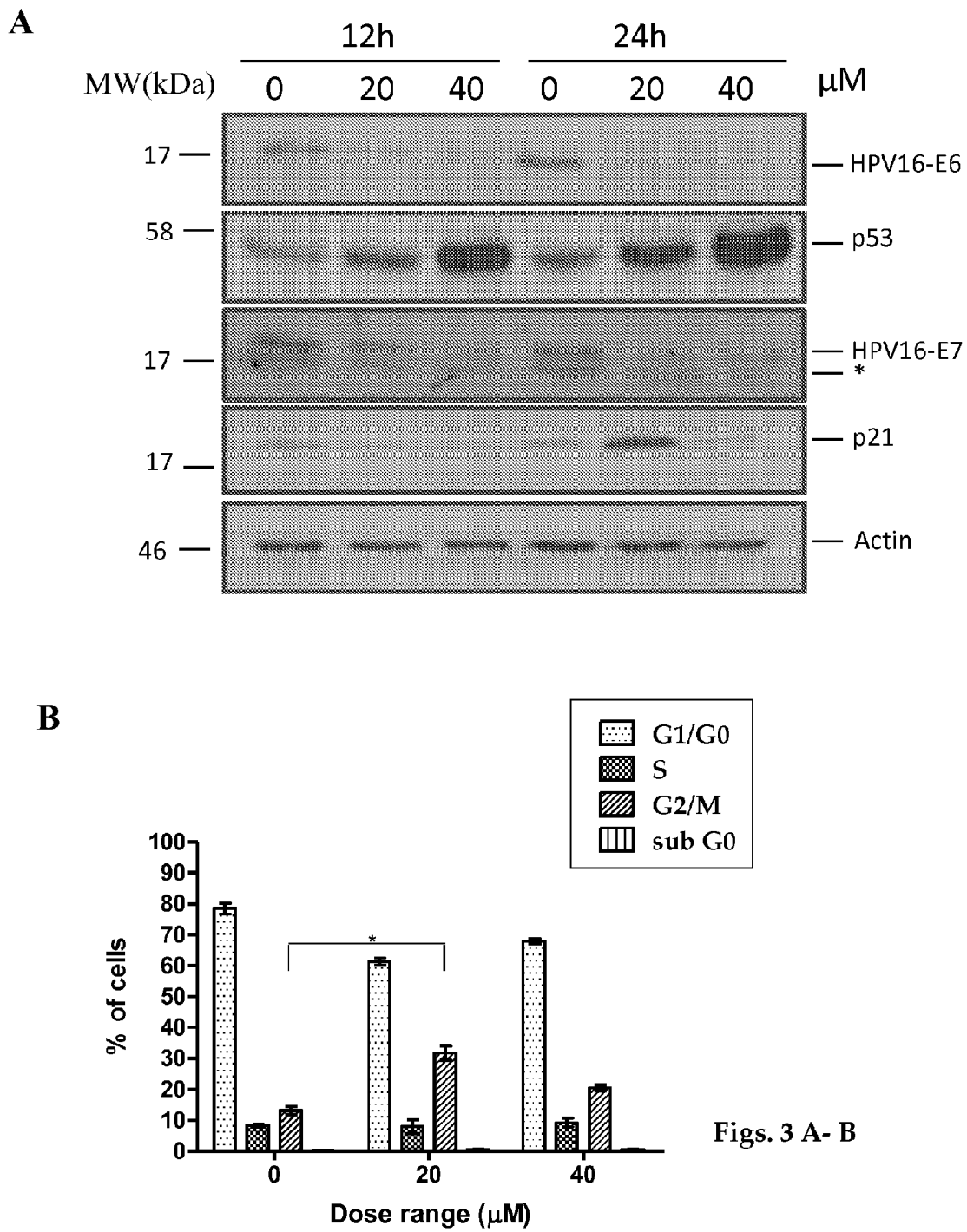
Figs. 3 A-B

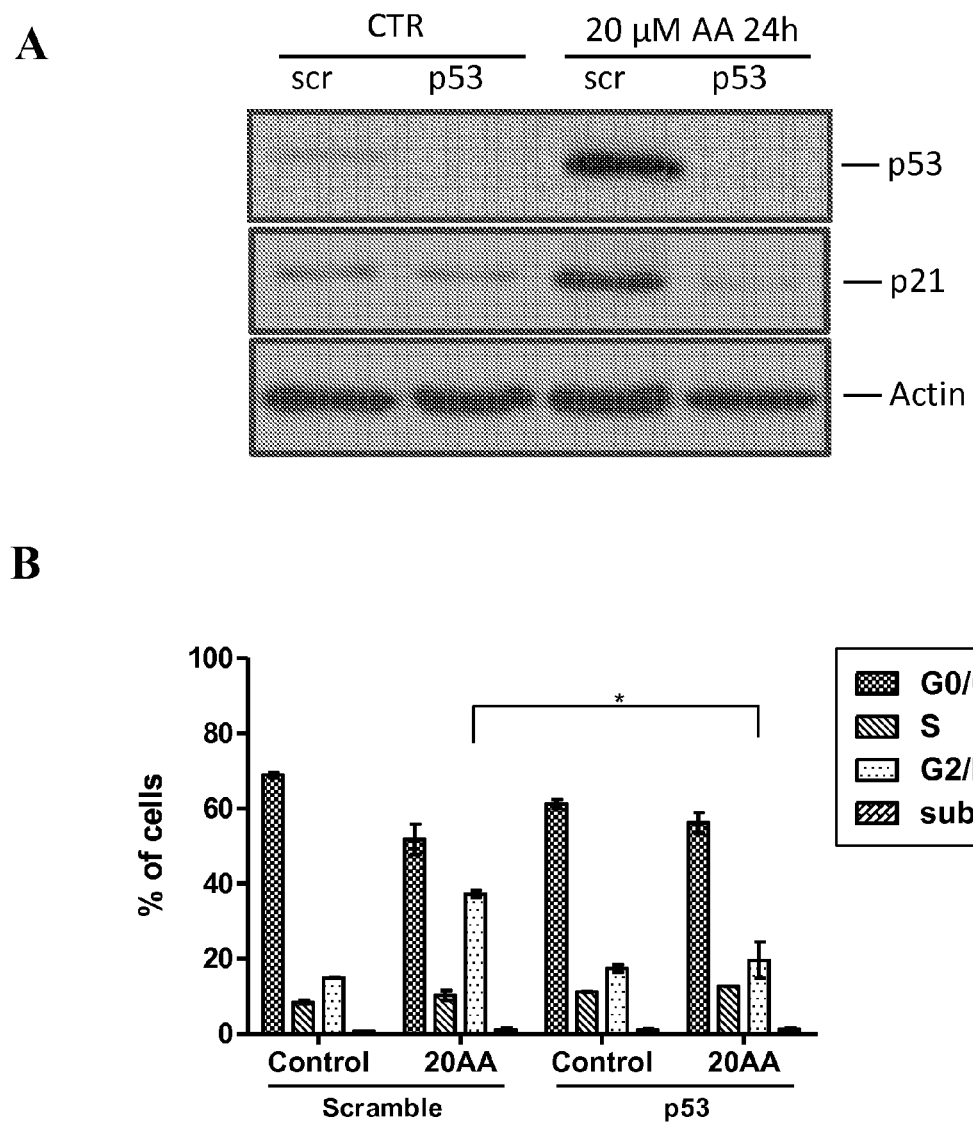
Figs. 4 A- B

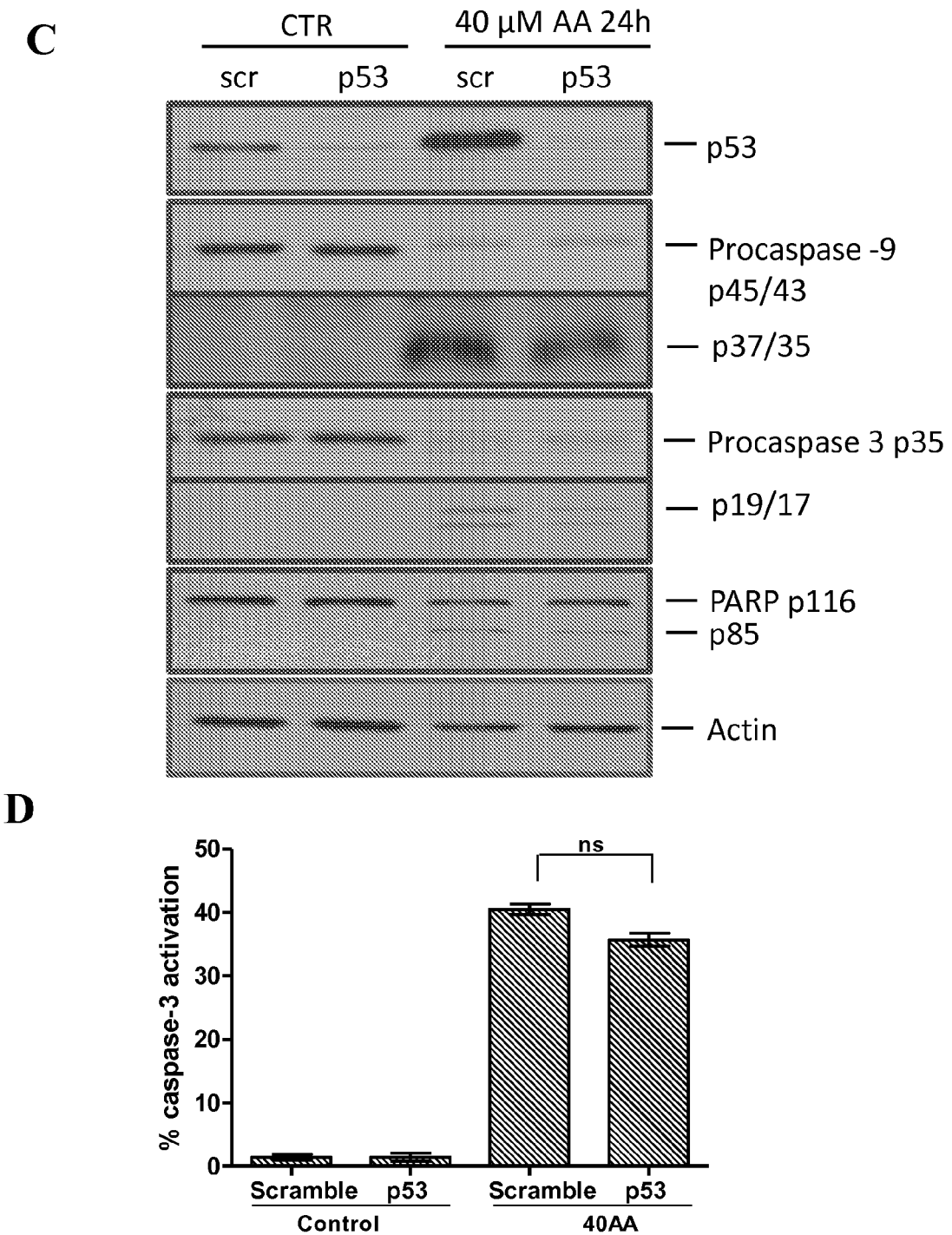
Figs. 4 C-D

E
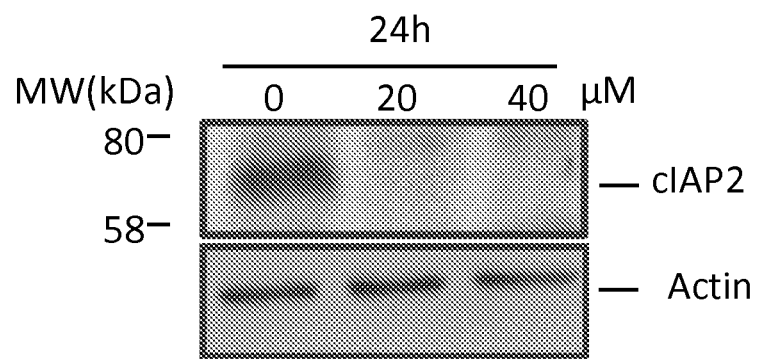
F
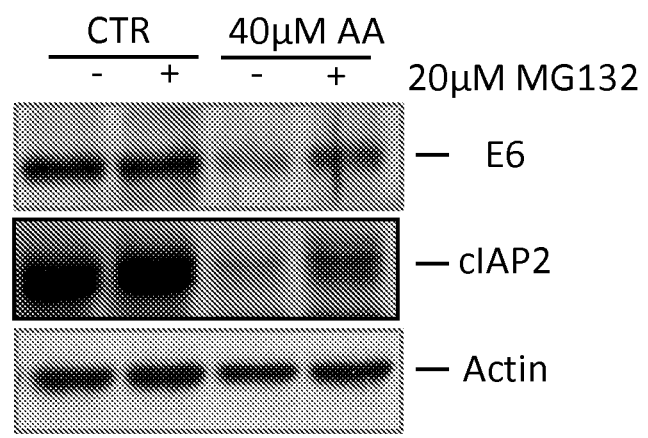
Figs. 4 E- F

A
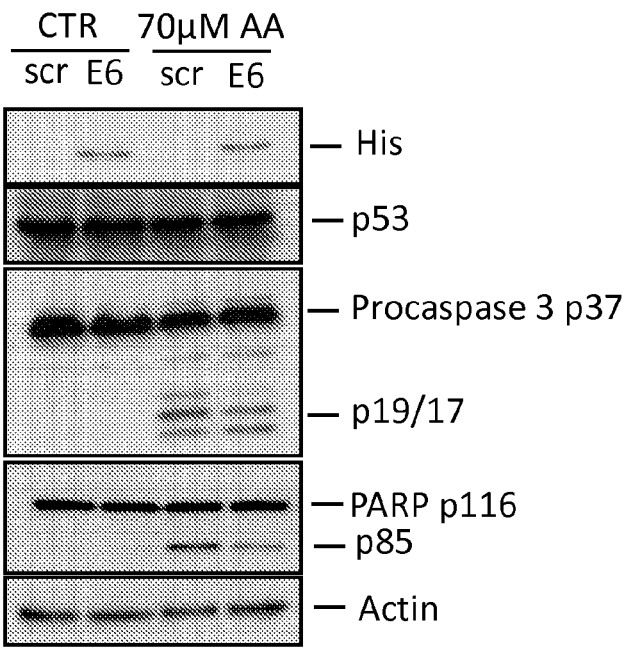
B
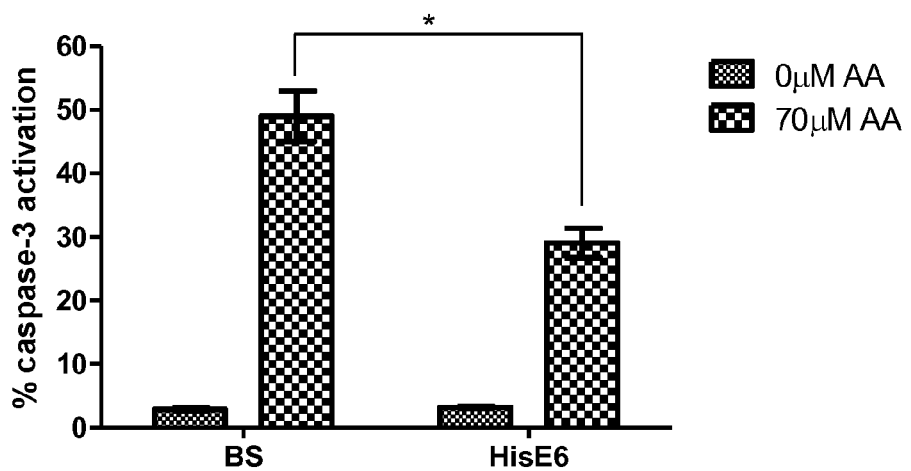
Figs. 5 A- B

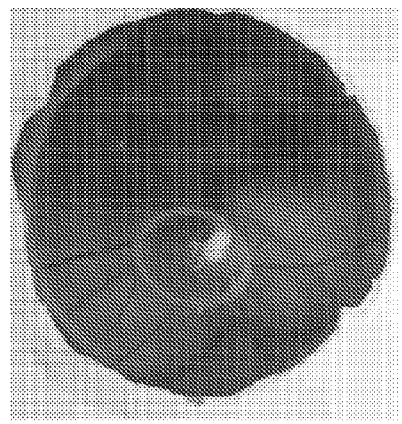
Control (SiHa) – 2 million cells
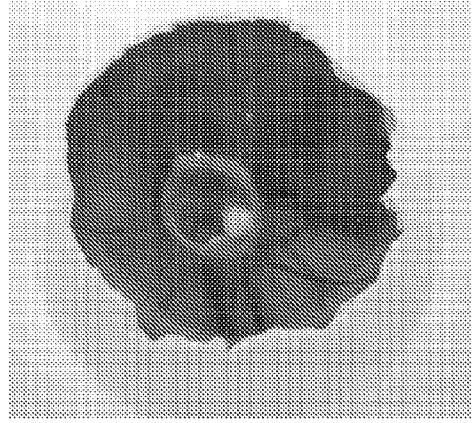
Emulsion control
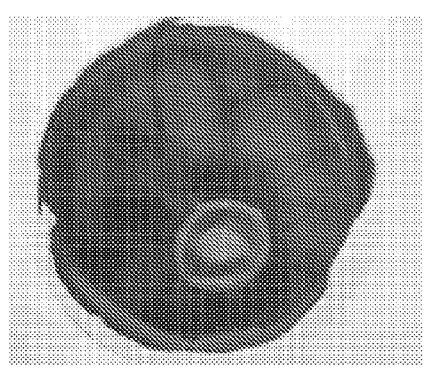
AA Emulsion – 4 mg/kg
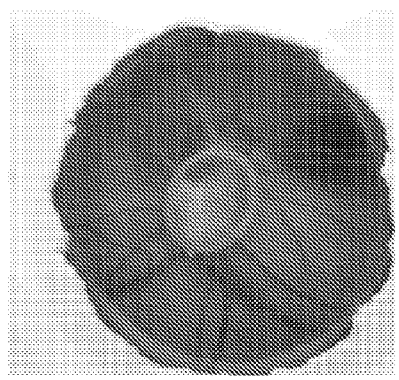
AA Emulsion – 8 mg/kg
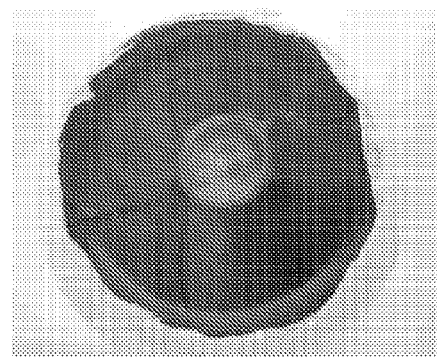
AA Emulsion – 12 mg/kg
Fig. 8

PHARMACEUTICAL COMPOSITIONS OF ANISOMELIC ACID AND THE USE THEREOF

BACKGROUND OF THE INVENTION

1. Field of the Invention

The present invention relates to a novel use of a compound, Anisomelic acid (AA) isolated from *Anisomeles malabarica*. In particular, the present invention concerns pharmaceutical compositions of Anisomelic acid. The present invention also discloses the use of Anisomelic and compositions thereof in anti-viral cancer therapy.

2. Description of Related Art

Cervical cancer is the second most frequent malignancy affecting women worldwide, with approximately 500,000 new cases diagnosed and 280,000 deaths each year. Although surgery and chemo-radiotherapy can cure 80-95% of women with early stage cancer and 60% of loco-regionally advanced cancer, the recurrent and metastatic disease remains the major cause of cancer death. The current cytotoxic treatment options for advanced and metastatic cancer demonstrate modest results, with response rates of maximum 30% and overall survival of less than 10 months. Given this limited degree of success with conventional therapies, interest has increased in other therapeutic alternatives for cervical cancers.

Most cervical cancers are caused by infection with a range of high-risk 'oncogenic' Human Papilloma Virus (HPV) types, and it is now accepted that more than 99% of cervical cancer is initiated by HPV infection. Persistent HPV infections lead to a sequel of various grades of cervical dysplasia and also cervical cancer. The major high risk genotypes associated with cervical cancer are HPV 16 and 18, and these two together are responsible for approximately 70% of cervical cancers.

Integration of the HPV viral genome and expression of E6 and E7 viral proteins are critical steps in the development of this cancer. Elimination of the trophic sentinel response by E6 protein occurs through several important mechanisms. The best characterized mechanism involves the inactivation and degradation of the tumor suppressor p53. E6 undermines the tumor suppressor function of p53 through formation of a complex with a cellular protein called E6-associated protein (E6-AP). As a result, the G1/S and G2/M cell cycle checkpoints are lost, and the cell is susceptible to genomic instability that may allow for development of neoplasia.

High-risk E6 also activates telomerase which prevents the erosion of telomeres and allows the host cell to continue through many rounds of division without damage to the DNA. E6 has also been reported to activate nuclear factor kappa B (NF-κB) leading to enhanced expression of Inhibitor of apoptosis protein 2 (IAP2) in HPV16 E6-immortalized human oral keratinocytes and primary human airway epithelial cells. It has also been observed that depletion of c-IAP2 leads to cell death, suggesting that HPV16-induced c-IAP2 expression is necessary for maintenance of the immortalized phenotype.

A second gene that is expressed very early in HPV infection is E7. E7 protein is pivotal to maintenance of the viral genome following entry into the host cell, and one of the most important functions is its ability to bind to the retinoblastoma tumor suppressor (Rb) family of cellular proteins. E7 simulates the phosphorylation and inactivation of pRb by binding to and targeting it to the proteosome for degradation. E2F transcription factors are then free to carry the tumor cell into S-phase. E7 interacts with p21Cip and p27Kip, and so interferes with their ability to inhibit cyclin-cdk activity and subsequently the cell cycle. Thus, E7 protein plays a large role in the maintenance of a cellular environment hospitable for viral replication.

In the continuing search for agents that may treat or ameliorate the affliction of cancer, natural products have provided an endless supply of active compounds that are increasingly being exploited. Several plant-derived compounds are currently successfully employed in cancer treatment.

Anisomelic acid is a diterpenoid isolated from *Anisomeles malabarica* (L.) R. Br., a herb belonging to the family Labiatae. This plant, commonly called Malabar catmint, is recommended in ancient medicines for use in catarrh, intermittent fever, bowel disorder and cancer. Aqueous ethanolic (50%) extracts of the plant have been shown to possess anticancer activity.

So far, Anisomelic acid as such has not been suggested or used for anti-viral cancer treatment.

SUMMARY OF THE INVENTION

The present invention is based on the finding that AA exhibits good efficiency in inducing apoptosis in HPV16 positive cervical cancer cells. It does not induce apoptosis effectively in non cervical cancer cells and also in non-cancerous MEF cells.

Surprisingly it has been found that AA inhibits protein level expression of E6 and E7, and thus is capable of acting as an anti-HPV agent.

It has also been found that AA induces p53-independent apoptosis primarily by down-regulation the cellular inhibitor of apoptosis 2 (cIAP2) protein resulting in intrinsic activation of apoptotic caspases.

Results obtained in connection with the present invention reveal AA as a compound with a novel mechanism of action that restores p53-mediated growth arrest and induces apoptosis in cervical carcinoma cells.

To the inventors' knowledge, this is the first disclosure of AA as an inhibitor of viral oncoprotein expression and as a chemotherapeutic agent for Human Papilloma Virus (HPV)-induced carcinoma. Due to the general importance of the role of E6/E7 oncoproteins and cIAP2 protein in cancer, said compound and derivatives thereof can be used more broadly in anti-cancer and anti-viral therapies.

Based on these findings, the present invention provides for pharmaceutical compositions of Anisomelic acid and salts thereof for use in anti-cancer therapy, in particular cervical cancer, in mammals, including humans and animals.

Furthermore, the present invention provides for improved compositions of Anisomelic acid and salts thereof in the form of emulsions or precursors thereof, in particular oil-in-water based microemulsions or precursors thereof.

The present invention also provides for the use of Anisomelic acid and salts thereof in the form of emulsions, optionally formed in vivo, in anti-viral cancer therapy and for improved method of anti-viral cancer therapy comprising the steps of administering to a mammal an efficient amount of Anisomelic acid or salts thereof.

More specifically, the pharmaceutical compositions for use in anti-viral treatment of cancer according to present invention are mainly characterized by what is stated in the characterizing part of claim 1.

The compositions according to a preferred embodiment of the invention are characterized by what is stated in the characterizing part of claim 9, and the method of treating a mammalian object is characterized by what is stated in the characterizing part of claim 15.

Considerable advantages are obtained by means of the present investigation.

The present invention discloses that Anisomelic acid, already as such, is an efficient inhibitor of HPV16-E6 and E7 oncoproteins expressed in cervical cancers. Anisomelic acid induces both cell cycle arrest and apoptosis in cervical cancer cells, which will enable its use as a drug to arrest cancer cell proliferation and also to kill cancer cells. The capability of Anisomelic acid to induce apoptosis independently of p53 offers an advantage in using it in treatment of p53-mutated or p53-null cancer types. The commercial use of Anisomelic acid can further be broadened to treat other HPV-related infections such as skin warts and genital warts.

In one preferred embodiment, Anisomelic acid is used in the form of an emulsion. The results obtained in connection with the invention show that the solubility and delivery of Anisomelic acid can be improved by preparing the pharmaceutical composition in the form of an emulsion or in the form of a mixture which forms an emulsion upon administration or in vivo, thus increasing the therapeutic usage of the compound.

Thus, as discussed below in more detail, Anisomelic acid in the form of an emulsion was tested for its effect to induce apoptosis in SiHa cells at 24 and 48 h. It was observed that Anisomelic acid induced apoptosis very efficiently compared with Anisomelic acid only. The apoptosis induction at 24 h and 48 h by Anisomelic acid emulsion was higher than Anisomelic acid. The maximum percentage of apoptosis induced by Anisomelic acid emulsion was achieved at 24 h itself whereas for Anisomelic acid it takes 48 h. This clearly shows that Anisomelic acid emulsion improved the drug bioavailability and efficient transfer of the drug into the cells which led to the higher percentage of apoptosis at 24 h itself. The emulsion was itself not toxic to the cells.

CAM inoculated tumors were treated with only emulsions or Anisomelic acid emulsions topically for 5 days with different concentrations. The results show that Anisomelic acid emulsion treatment did not allow the development of tumors and suppressed it. This provides good evidence for the efficacy on Anisomelic acid emulsion in an alternative in vivo CAM model.

Next the novel technology will be examined more closely with the aid of a detailed description with reference to the attached drawings.

BRIEF DESCRIPTION OF THE DRAWINGS

FIG. 1A shows the representative phase contrast microscopy images of 0 and 40 µM Anisolemic acid (AA) treated cells at 48 h time point. FIG. 1B shows the caspase-3 activation by AA at an increasing dose range. FIG. 1C shows that AA at high doses does not inflict necrotic cell death. FIG. 1D shows the effect of AA in HPV positive HeLa and Caski cells (p53+) where it induces apoptosis and in HPV negative c33a cells (p53−) where the apoptotic induction is very less. FIG. 1E shows that AA failed to induce effective apoptosis in breast cancer cells MCF7 cells (p53+) and MDA-MB-231 (p53−). FIG. 1F shows that AA failed to induce cell death at 40 µM in the non-cancerous MEF cells.

FIG. 2A demonstrates that AA induced the cleavage of pro-caspase 8, 9, 3 and poly-ADP-ribose polymerase (PARP), which is a substrate of caspase-3. FIG. 2B illustrates that mitochondrial membrane depolarization occurred in a time-dependent manner in response to 20-40 µM AA.

FIG. 3A shows that p53 was significantly stabilized in a dose- and time-dependent manner in response to AA treatment. Concomitantly, the E6 viral protein was down-regulated. In a similar manner, the expression of E7 protein was also down-regulated after 12 h AA treatment, but a clear induction of p21 protein was seen only after 24 h with 20 µM AA. On the other hand, 40 µM AA did not induce p21 expression. FIG. 3B demonstrates the cell cycle analysis of synchronized cells with or without AA treatment. AA leads to the accumulation of cells at the G2/M phase after 24 h treatment. The G2/M arrest occurred more effectively at 20 µM AA dose and it coincided with the observed p21 induction.

FIG. 4A shows the significance of p53 in AA-induced apoptosis and cell cycle arrest, p53 expression was down regulated using p53-shRNA. Western blot analysis of p53 and p21 revealed that induction of these proteins by 20 µM AA was abrogated in the cells in which p53 was down-regulated. FIG. 4B confirms that the absence of p53 led to reversal of AA-induced cell cycle arrest as the cells no longer accumulated at the G2/M phase 24 h after start of the treatment. FIG. 4C shows that suppression of p53 protein by shRNA did not inhibit AA-induced apoptosis since 40 µM AA treatment resulted in cleavage of caspase-9, caspase-3 and PARP even in the absence of p53 expression. FIG. 4D shows that there was no significant decrease in the percentage of apoptotic cells in the absence of p53. FIG. 4E shows the downregulation of cIAP2 protein level by AA treatment. FIG. 4F shows that AA-mediated downregulation of E6 and cIAP2 proteins are mediated by a proteasome pathway, where the cells when treated with proteasome inhibitor MG132, inhibited the degradation of E6 and cIAP2 proteins.

FIG. 5A shows transfection of E6 rescued c33a cells from apoptosis. FIG. 5B shows reduction in the percentage of induced apoptosis.

FIG. 8 shows the effect of AA emulsion in SiHa tumors implanted on CAM.

DETAILED DESCRIPTION OF PREFERRED EMBODIMENTS

Figure 6:
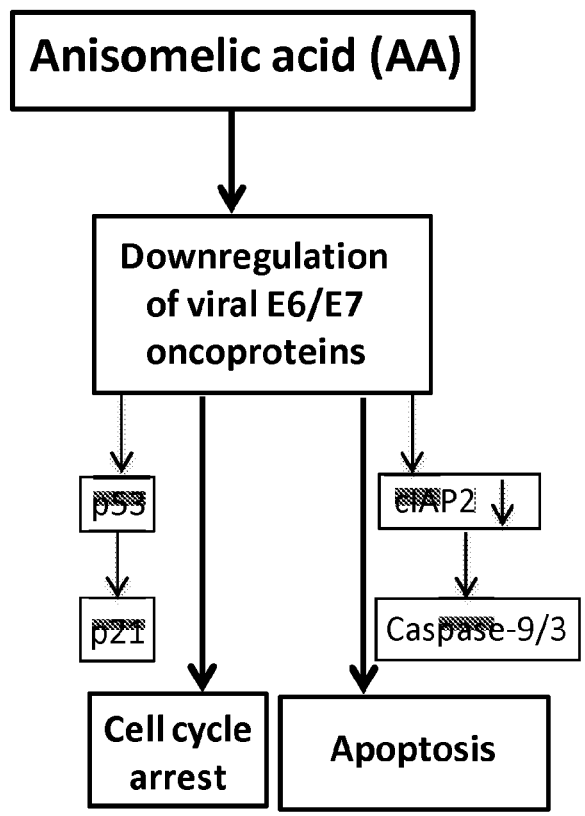
FIG. 6 outlines the proposed model for the mechanism of action of AA.

As discussed above, the present invention is based on the finding that Anisomelic acid and salts thereof are efficient in down-regulating viral oncoproteins E6 and E7 and, in particular they also induce p53 dependent cell cycle arrest and p53 independent apoptosis by down-regulating cIAP2.

In particular, AA exhibits good efficiency in inducing apoptosis in HPV16 positive cervical cancer cells at 40 µM while it does not induce apoptosis effectively in non cervical cancer cells and also in non-cancerous MEF cells.

Anisomelic acid (and salts thereof) is even more efficient when prepared as an emulsion. Results obtained both in vitro and in vivo support this conclusion.

Within the scope of the present invention the abbreviation "AA" stands for Anisomelic acid. Anisomelic acid has the general formula I:

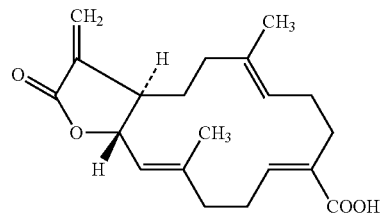

Its CAS number is 59632-76-7.

Included in the concept and covered wherever appropriate by the abbreviation "AA" are also pharmaceutically acceptable salts of Anisomelic acid and any derivatives of the acid which has a similar activity. Racemates as well as optical isomers of AA and its derivatives are also included herein.

As used herein, the term "pharmaceutically acceptable salts" refers to salts or zwitterionic forms of Anisomelic acid. Salts of the Anisomelic acid can be prepared for example during isolation and purification of the acid or separately by reacting the acid with a compound having a suitable cation. Suitable pharmaceutically acceptable cations include alkali metal (e.g., sodium or potassium) and alkaline earth metal (e.g., calcium or magnesium) cations.

For the purpose of the present technology, Anisomelic acid is used in essentially pure form, i.e. at a purity of at least 70%, preferably at least 75%, more preferably at least 85%, advantageously at least 95%, suitably at least 98% and in particular at least 99.5%, or even 99.95%, by weight (of the active ingredient of the pharmaceutical composition). AA can be obtained by extraction of natural raw-materials containing said compound or it can be used as a synthetic compound, the latter being particularly preferred. Some alternative ways of providing AA will be discussed below.

AA can be obtained by methods per se, for example by isolation from *A. malabarica, A. indica* or *A. ovata*. Thus, in one embodiment, the method described by Arisawa et al., 1986 can be employed: The whole plant is shade-dried, powdered and extracted with 90% methanol in a soxhlet apparatus, then vaccum-dried. The methanolic crude extract was partitioned between chloroform and water. The chloroform layer was concentrated and partitioned between 90% methanol and petroleum ether. The 90%, ethanolic extract was concentrated and subjected to silica gel column chromatography which will yield different compounds and one of them is anisomelic acid. It is obtained as colorless crystalline prisms, with melting point around 148-150° C. and molecular formula is $C_{20}H_{26}O_4$.

Marshall's synthesis of dl-anisomelic acid (Marshall & DeHoff 1987; Marshall & DeHoff 1986) makes use of a 2-selective Horner-Emmons condensation in the key cyclization step.

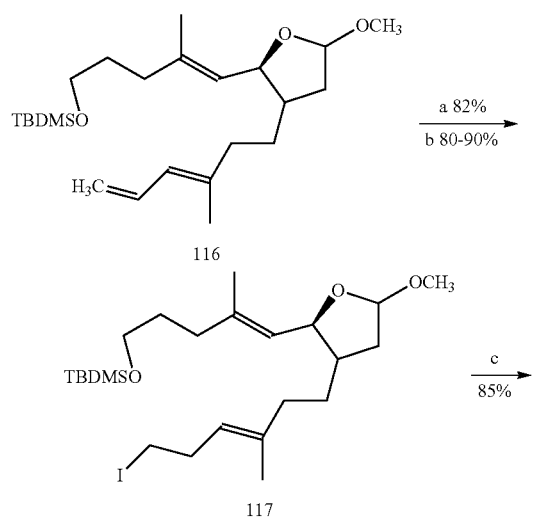

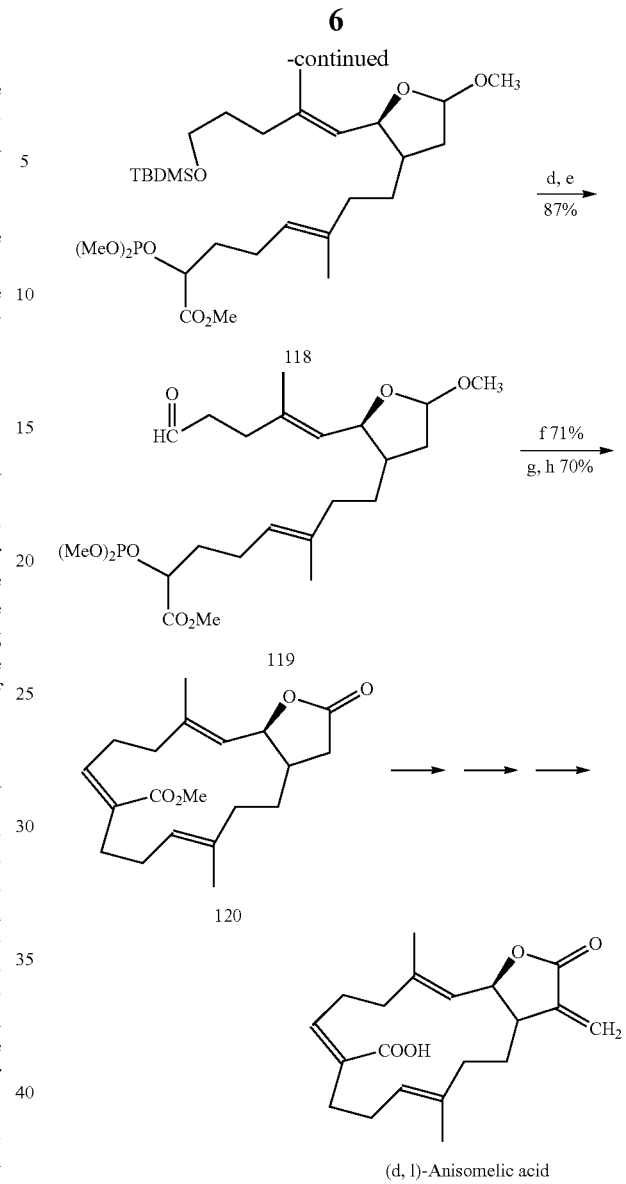

Tius 1988

Selective hydroboration of the terminal alkene linkage in 116 with disiamylborane, followed by basic peroxide, provides an alcohol that is converted to the corresponding iodide with iodine and triphenylphosphine in the presence of imidazole. Displacement of the iodide with the sodium salt of methyl (dimethylphosphono) acetate produces 118 in 85% yield. Cleavage of the silyl ether of 118 is accomplished with methanolic pyridinium tosylate at reflux. Swern oxidation furnishes aldehyde 119. Initially, the intramolecular Horner-Emmons reaction was accomplished with sodium hydride in DME in the presence of 18-crown-6 ether. The success of this reaction is found to be highly dependent upon the conditions. A yield of 71% (Z/E=95/51 is achieved through the use of the Masamune-Roush conditions. Cyclic acetal hydrolysis with aqueous pyridinium tosylate (PPTS) followed by oxidation with PCC furnishes lactone ester 120 in 70% yield. This compound is converted to dl-anisomelic acid. It is interesting that 120 is obtained as the 2 geometrical isomer. The reason for the selectivity, which is opposite of what has been observed for 115, 112, and 110, has not been discussed. It is worth noting that solvent effects have been found to have a strong influence on the E/Z ratios of products from the reaction of stabilized Wittig reagents with aldehyde.

AA treatment led to efficient apoptosis in HPV positive cervical cancer cells by down-regulating the viral oncoproteins and cellular inhibitor of apoptosis protein 2 (cIAP2). These events precede mitochondrial membrane depolarization, and cleavage of caspase-9, caspase-3 and PARP, all typical features of apoptotic cell death.

To the best of the inventors' knowledge, this is the first report to provide direct experimental evidence of the molecular mechanism behind AA-induced apoptosis in SiHa cervical cancer cells. The results, thus, provide new insights into the possible molecular mechanisms of anisomelic acid, in addition to its new use as an antitumor agent.

Restoration of cell cycle arrest by therapies directed against the viral proteins E6 and E7 represent, in one embodiment, an effective and pragmatic approach. Cell division is prevented. This also leads to the perception of the competency of AA to induce apoptosis independently of p53 that might offer an advantage in p53-mutated or p53 null anticancer therapy. In essence, the results justify the use of anisomelic acid as an anti-cervical cancer and anti-HPV compound.

The present invention provides for therapeutic applications which comprise AA, in particular AA in isolated, or in isolated and purified form, for the treatment of cancer.

Anisomelic acid is a hydrophobic compound which dissolves in DMSO and hot ethanol, and is mostly insoluble in water or other aqueous solvents. Low aqueous solubility of drugs is a serious concern as it leads to poor bioavailability, high intrasubject/intersubject variability and lack of dose proportionality. Hence, for successful delivery of drugs both orally and also by other means it is necessary to improve the solubility.

The present invention provides for various approaches for this purpose like solid dispersion, anti-solvent, complexation with cyclodextrin and lipid-based formulations. There are various lipid-based emulsion delivery systems and one of them is self-microemulsifying drug delivery systems (SMEDDS). SMEDDS is defined as isotropic mixtures of natural or synthetic oils, solid or liquid surfactants, or alternatively, one or more hydrophilic solvents and co-solvents/surfactants that have a unique ability of forming fine oil-in-water (o/w) micro emulsions upon mild agitation followed by dilution in aqueous media, such as GI fluids.

SMEDDS spreads readily in the GI tract, and the digestive motility of the stomach and the intestine provide the agitation necessary for self-emulsification.

The SMEDDS mixture can be filled in either soft or hard gelatin capsules. A SMEDDS formulation according to the present invention comprises oils, surfactants and if required an antioxidants. Co-surfactants and co-solvents can be added to improve the formulation characteristics. Anisomelic acid emulsions are prepared and tested for its efficacy in inducing apoptosis.

Thus, in one embodiment, Anisomelic acid is dissolved in a hot ethanol to form a mixture and the is dissolved in a surfactant or in a mixture of a surfactant, poly(ethylene glycol) and an oil. The ratio between the liquid components can vary between 1 part by weight of the alcohol to 100 parts by weight of the mixture formed by the surfactant, PEG and oil to 100 parts by weight og the alcohol to 1 part by weight of the mixture. Preferably the ratio is about 1 part of alcohol to 5 parts by weight of mixture—5 parts by weight of alcohol to 1 part by weight of mixture, for example about 1-2 parts by weight to 0.5 to 1 part by weight of the components in the earlier indicated order.

In view of the chemical properties of the compound, as AA is a diterpenoid, like paclitaxol, a well-known anti-tumor agent, AA can be administered topically, parenterally, intraperitoneally or intravenously. AA emulsions can be administered orally.

The active components are used in effective amounts. The route of administration, the dosage as well as the exact formulation are chosen depending on the subject's condition. Thus, the interval can be adjusted individually to provide levels of the active compound in the blood plasma that are sufficient to maintain and obtain the desired therapeutic effects.

In general, however, doses employed for humans typically are in the range of 0.001 mg/kg to about 1000 mg/kg per day, preferably in the range of about 0.1 mg/kg to about 500 mg/kg per dose of inhibitor. Typically, AA is administered at 0.001 to 100 mg/kg body weight, for example at 0.01 to 50 mg/kg body weight. In some embodiments, AA can be employed in doses ranging from about 0.1 to about 50 mg/kg, about 0.5 to about 40 mg/kg or about 0.7 to about 30 mg/kg. Specific doses contemplated include sub-ranges of any of the foregoing ranges in 0.1 mg/kg increments.

The pharmaceutical composition will comprise AA either as the primary or as the sole therapeutically efficient component (or agent). Therefore, within the scope of the present technology, compositions are also provided wherein the effective agent consists of or consists essentially of Anisomelic acid and salts thereof. Naturally, it is possible to combine AA with other anticarcinogenic compounds, such as tyrosine kinase inhibitors, such as Pazopanib, and angiogenetic agents, such as vascular endothelial growth factor inhibitors, e.g. Bevacizumab.

The pharmaceutical compositions can be in any suitable form. Typical pharmaceutical forms include aqueous, oleaginous suspension, dispersions as well as sterile powders, which may be used for the extemporaneous preparation of injectable solutions or dispersions. It can be used for topical (e.g. intravaginal) application, for example in the form of intravaginal creams or by application of prolonged release solid preparations, such as sustained release pharmaceutical plasters. The compositions may also be solutions or suspensions in non-toxic diluents or solvents, e.g. as solutions in 1,3-butanediol. Alternatively, they can be prepared as microemulsions and administered, for example orally.

The carrier can be a solvent or dispersion medium containing, for example, water, polyol (for example, glycerol, propylene glycol, and liquid polyethylene glycol, and the like), ethanol, and mixtures of the indicated components, various vegetable oils, Ringer's olution and isotonic sodium chloride solutions. In addition, fixed oils may be employed as a solvent or suspending medium. Fixed oils that can be employed include synthetic mono- or diglycerides. Further, fatty acids such as oleic acid find use in the preparation of injectables.

As conventional, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition.

The pharmaceutical compositions can also be selected for inhalation or for delivery through the digestive tract, such as orally. The preparation of such pharmaceutically acceptable compositions is within the skill of the art. AA can be present in the same pharmaceutical composition. They can also be comprised in different pharmaceutical compositions which are, for example, supplied in the same package.

Although the above description primarily relates to human objects, pharmaceutical compositions for veterinary use are also included herein.

The following non-limiting example illustrates an embodiment of the invention.

EXAMPLE

The experimental results presented below demonstrate that AA depletes the viral oncoproteins E6/E7 and cellular inhibitor of apoptosis protein 2 (cIAP2) thus, inducing apoptosis in SiHa HPV16 positive cervical cancer cells. AA also activates the p53-p21 pathway leading to G2/M cell cycle arrest.

The results show that AA emulsion induced apoptosis more efficiently at an earlier time point compared with AA only. AA emulsion was also efficient in suppressing the growth of tumours in CAM model.

Mammalian models are frequently used for preclinical evaluation of new drug delivery systems (DDS). However, valid mammalian models are expensive, time-consuming, and not easy to set up and evaluate. Furthermore, they are often linked to administrative burden with respect to ethical and legal aspects. Hence we use chorioallantoic membrane (CAM), as an alternative to mammalian models for the evaluation of DDS. Features of the CAM, the anatomy of the embryo, and the blood were investigated to assess properties of the drug carriers such as toxicity and biocompatibility, as well as the activity, toxicity, biodistribution and pharmacokinetics of the drug. The simplicity, rapidity, and low cost of the different assays that can be performed with chick embryos strengthen the interest of routinely using this model in pharmaceutical technology research.

The chorioallantoic membrane provides an excellent natural substrate for all types of tumor cells. During the development of drug delivery system, chick embroys can be used to evaluate the activity or toxicity of a drug on both the CAM and CAM-grafted tumors. Administration of drug routes on human, topical, intravenous (IV), and intraperitoneal (IP) administration can be used on chick embroys. Because of the low cost and simplicity of the assays with the chick embryo, this model offers the possibility of performing a high-throughput screening of drug delivery system before using mammalian models. Being naturally immunodeficient, the chick embryo represents an alternative model system for the evaluation of drug delivery system. The growth of SiHa tumor cells in the CAM has already been well established and the efficacy of the AA emulsion by treating the tumors topically for 5 days was tested.

Materials and Methods

AA was isolated from *Anisomeles malabarica* as previously described by Arisawa et al., 1986 with few modifications. A 100 mM stock solution was prepared in DMSO at room temperature.

SiHa, HeLa, Caski and c33a cervical cancer cells and Mouse Embryonic Fibroblasts (MEF) were cultured in DMEM (Sigma-Aldrich, St Louis, Mo., USA). MCF7 and MDA-MB-231 breast cancer cells were cultured in RPMI (Sigma-Aldrich). The medium was supplemented with 10% fetal calf serum (BioClear, Wiltshire, UK), 2 mM L-glutamin, 100 U/ml penicillin, 100 µg/ml streptomycin (Sigma-Aldrich).

Assessment of Cell Death and Mitochondrial Depolarization

SiHa cells were treated with 0-50 µM AA or solvent control at 10 µM interval. The dose range was limited to 50 µM since our preliminary studies showed ≥95% killing at 50 µM (MTT cytotoxicity assay, unpublished data). Fourty eight hours later, the cells were collected and analyzed for apoptosis and/or necrosis. Activated caspase-3 in cells was labeled with phyco-erythrin-conjugated antibody according to manufacturer's protocol (PE Active Caspase-3 Apoptosis Kit; BD Pharmingen, San Diego, Calif.) and analyzed by FACSCalibur flow cytometer (FL-2, FSC, BD Pharmingen).

SiHa cells were also tested with 40 µM AA and AA emulsion for 24 and 48 h. The cells were collected and analyzed for apoptosis adopting PE active caspase-3 assay by FACS.

For detection of permeabilized (necrotic) cells, the cells were trypsinized and resuspended in 50 µg/ml Propidium Iodide (PI) (Sigma-Aldrich) in PBS for 10 minutes at room temperature. The samples were analyzed by flow cytometry.

Tetramethylrhodamine, methyl ester (TMRM, Invitrogen, Cergy Pontoise, France) was stored as 20 mM dimethylsulfoxide stock and diluted in medium before use. The cells were incubated in 20 nM tetramethylrhodamine for 10 min in 37° C. water bath. The cells were placed on ice and analyzed immediately by FACSCalibur flow cytometry.

HeLa, Caski, c33a, MCF7, MDA-MB-231 and MEF cells were treated with 0 and 40 µM AA. Forty eight hours later, the cells were collected and analyzed for apoptosis.

Cell Cycle Analysis

Cells were synchronized by serum-starvation (1% serum) for 48 h and then cultured in medium containing 10% FCS for 24 h. After this, the cells were incubated with 0, 20 and 40 µM AA for 24. These doses were chosen since apoptosis induction was highest at 40 µM (the dose was limited to 40 µM in the following studies). The cells were collected and disrupted and the nuclei labelled for DNA content with PI by re-suspension in sodium citrate buffer [40 mM Na-citrate, 0.3% Triton X-100, 50 µg/ml PI (Sigma-Aldrich)]. After incubation at room temperature for 10 min, the samples were immediately analyzed by FACSCalibur flow cytometry.

RNA Interference

The pSUPER vector (Oligoengine, Seattle, Wash., USA) for expression of human p53 targeted shRNA (5'GACUCCA-GUGGUAAUCUACUUCAAGAGAGUAGA-UUACCACUGG AGUCUU3', Brummelkamp et al., 2002) was kindly provided by Dr. Pia Roos-Mattjus. The scramble (Scr) pSUPER vector (5'GCG CGC TTT GTA GGA TTC G3', Ostling et al., 2007) was transfected to control cells. Trypsinized SiHa cells were transfected with the shRNA expression plasmids by electroporation in Opti-MEM media (Gibco, Calif., USA). Twenty four hours post-transfection, the culture medium was changed and the cells were treated with AA or left untreated, after which the cells were cultured for another 24 h or 48 h. The efficiency of the shRNA expression vector was determined by Western blotting for p53 expression.

Plasmid Transfection c33a cells were pelleted and resuspended in OPTIMEM (Gibco, Invitrogen Foundation, Washington D.C., USA) and electroporated with mock or His-tag E6 plasmid at 220 V and 975 µF. Twenty four hours post-transfection, the culture medium was changed and the cells were treated with AA or left untreated, after which the cells were cultured for another 24 h or 48 h for further analysis adopting Western blotting and cell death assay by FACS.

Western Blotting

Whole cell lysates were prepared by lysing the cells in Laemmli sample buffer (Laemmli, 1970) and boiling the samples for 10 min after which proteins were separated in 12.5-15% SDS-PAGE. Western blotting was performed using antibodies against poly (ADP-ribose) polymerase (clone C-2-10; Sigma-Aldrich), Bid, Bax, caspase 8, caspase 9, caspase 3, SAPK/JNK, Phospho SAPK/JNK (Thr183/Tyr185), cIAP2 (Enzo Lifesciences), Akt, Phospho Akt(Ser473) (Cell Signalling Technology, Davers, Mass., USA), p21, Bcl-xL (Santa Cruz Biotechnology, Inc, Santa Cruz, Calif.), β-actin (clone AC-40; Sigma-Aldrich) and p53 (clone DO-1; BD Pharmingen). Horseradish peroxidase-conjugated secondary antibodies were obtained from Southern Biotechnology Associates (Birmingham, Ala.), Promega (Madison, Wis.) and Amersham Biosciences (Freiburg, Germany). The results were visualized using the ECL method (Amersham Biosciences) on X-ray film. The presented Western blot results are representative of at least three independent experiments.

Preparation of AA Emulsion

Anisomelic acid was dissolved in hot ethanol and this mixture was dissolved in Tween 30:PEG400:Olive oil in the ration of 4:1:1:1

Testing of AA Emulsion in CAM Tumors 2 million SiHa cells were mixed with Matrigel in 1:1 ratio and the mixture was implanted on the CAM membranes on the $8^{th}$ day of embryo development. The CAM with tumors were treated with ethanol (control), emulsion with or without AA after one day of the cancer cells inoculation till five consecutive days. After five days of drug treatment the tumors were photographed.

Results

In order to examine the mechanism underlying the previously reported cytotoxicity of AA, we investigated if AA would induce apoptotic death of cultured SiHa cervical cancer cells. Representative phase contrast images of AA-induced cell death are shown in FIG. 1A. We then incubated the cells with 0-50 μM AA for 24 and 48 hours, and determined the percentage of cells that contained activated caspase-3 as a measure of apoptosis. A marked activation of caspase-3 was observed after 48 h at 40 μM AA (FIG. 1B). Pre-incubation of SiHa cells with 40 μM Z-VAD.fmk, a broad range caspase inhibitor, prior to 40 μM AA treatment reversed caspase-3 activation and apoptotic cell morphology, thus confirming the role of caspases in AA-induced cell death (data not shown). Interestingly, AA doses greater than 40 μM reduced caspase-3 cleavage dramatically (FIG. 1B). As we could not detect increased cell permeabilization by PI labeling at this higher dose range (FIG. 1C), it is not likely that that AA would induce necrotic cell death, but could trigger caspase-independent cell death or cellular senescence. Since the best induction of apoptosis was obtained at 40 μM AA, we limited our further studies to 0-40 μM AA.

We also tested the effect of AA in other cervical and breast cancer cell lines at 0 and 40 μM. As seen in the FIG. 1D, AA effectively induced apoptosis in HPV positive HeLa and Caski cells (p53$^+$) whereas the apoptosis induction in HPV negative c33a cells (p53) were significantly less. AA also failed to induce effective apoptosis in breast cancer cells MCF7 cells (p53$^+$) and MDA-MB-231 (p53−) (FIG. 1E). AA also failed to induce cell death at 40 μM in the non-cancerous MEF cells (FIG. 1F).

To investigate the execution route of the observed apoptosis, we examined if AA would also promote mitochondrial membrane depolarization, a good activation marker of the intrinsic apoptotic signaling pathway. Mitochondrial membrane polarity was evaluated by tetramethylrhodamine (TMRM) labeling 8-48 h after the start of AA treatment. Indeed, mitochondrial depolarization occurred in a time-dependent manner in response to 20-40 μM AA (FIG. 2A). Lysates of AA-treated SiHa cells were analyzed for cleavage of caspase-9, caspase-8, caspase-3 and PARP. Cleavage of procaspase-9 into 35/37 kDa fragments was seen after 12 h incubation with 20 and 40 μM AA (FIG. 2B). Cleavage of procaspase-8, a death receptor-associated caspase, occurred later, as caspase-8-cleaved fragments were observed abundantly only after 24 h of AA treatment (FIG. 2B). These results suggest that AA primarily activates the intrinsic, mitochondrial pathway of apoptosis, associated with caspase-9 activation. Treatment with 20-40 μM AA also induced the cleavage of caspase-3 and poly-ADP-ribose polymerase (PARP), which is a substrate of caspase-3 (FIG. 2B). Overall, these results demonstrate that AA, in the dose-range of 20-40 μM, induces apoptosis through caspase-9 and caspase-3 activation.

SiHa cervical cancer cells have been transformed by high-risk Human Papilloma Virus (HPV). As E6 and E7 play such critical roles in SiHa cell transformation, the expression of these viral proteins as well as p53 and p21 was examined. Indeed, the E6 viral protein was down-regulated with corresponding stabilization of p53 protein (FIG. 3A). In a similar manner, the expression of E7 protein was also down-regulated after 12 h AA treatment, but a clear induction of p21 protein was only seen after 24 h with 20 μM AA (FIG. 3A). On the other hand, 40 μM AA did not induce p21 expression, which shows that low dose of AA induces p21, one of the p53 responsive genes. Similar results have been obtained in other studies showing that p53 cellular responses and targets varies depending on the dose of the insults. These results demonstrate that AA is capable of effectively inducing degradation of E6 and E7 viral proteins, thereby allowing release of p53 and p21 from E6 and E7 inhibition, respectively. Such prominent effects on p53 are expected to be reflected as a cell cycle arrest. Indeed, the cell cycle analysis of synchronized and AA treated cells accumulated at the G2/M phase after 24 hr treatment (FIG. 3B). The G2/M arrest occurred more effectively at 20 μM AA dose and it coincides with the observed p21 induction (FIGS. 3A and 3B).

In addition to its role in regulation of the cell cycle, p53 promotes apoptosis through the transcriptional activation of pro-apoptotic target genes, which are members of both intrinsic and extrinsic apoptotic pathways. To evaluate the significance of p53 in AA-induced apoptosis induction and cell cycle arrest, we down-regulated p53 expression using p53-shRNA. Western blot analysis of p53 and p21 revealed that induction of these proteins by 40 μM & 20 μM AA respectively, was abrogated in the cells in which p53 was down-regulated (FIGS. 4A & 4B). Consequently, the absence of p53 led to reversal of AA-induced cell cycle arrest, as the cells no longer accumulated at the G2/M phase 24 h after the start of AA treatment (FIG. 4C). These observations imply that the activation of p53 protein by AA treatment directly leads to expression of one of its transcriptional targets, p21, as well as G2/M phase arrest. The cell cycle arrest in response to AA treatment is clearly a p53-dependent process (FIG. 4C). Interestingly, suppression of p53 protein by shRNA did not inhibit AA-induced apoptosis since 40 μM AA treatment resulted in cleavage of caspase-9, caspase-3 and PARP even in the absence of p53 expression (FIG. 4A). These results were further verified by the flow cytometric analysis of caspase-3 activation in response to AA. We did not observe any significant decrease in the percentage of AA-induced apoptosis in the absence of p53 expression (FIG. 4D). This data clearly indicates that AA-induced apoptosis is p53-independent in the HPV-positive SiHa cell line. As stabilization of p53 was not observed to be essential for the induction of apoptosis, we speculated that apoptosis might be induced by inactivation of the effect of the IAP family members. It has been shown that cIAP2, in particular, is overexpressed in HPV16-E6 infected cells and seems to function as a critical and potent anti-apoptotic factor in these virally infected cancer cells. Indeed, we observed an AA-induced decline in the expression of cIAP2 protein occurring with similar kinetics as the downregulation of E6 oncoprotein (FIGS. 4E & 3A), which suggest that the p53-independent pathway to AA-induced apoptosis could be mediated by reduction in cIAP2 expression.

Also, to determine whether AA-mediated downregulation of E6 and cIAP2 proteins are mediated by a proteasome pathway, the cells were treated with proteasome inhibitor MG132 and analyzed by Western blotting. As seen from the results, MG132 inhibited the degradation of E6 and cIAP2 proteins after the treatment of AA (FIG. 4F)

To ascertain the role of E6 in AA-induced apoptosis, we transfected HPV negative c33a cells with mock and His-tag E6 plasmids, treated them with 0 and 70 μM AA and assayed the cells for AA-induced apoptosis adopting Western blot and FACS. Though c33a cells do not undergo apoptosis at 40 μM (FIG. 1D), they undergo apoptosis at a higher dose of 70 μM. As seen in FIG. 5, transfection of E6 rescued c33a cells from apoptsis significantly, thus confirming that AA-induced apoptosis is dependent on the down-regulation of E6. C33a cells have mutant p53, which is not affected by E6 transfection but the cleavage of caspase 3 and PARP are inhibited (FIG. 5A). The percentage of apoptosis induced is also significantly reduced (FIG. 5B).

A proposed mechanism for the molecular action of AA is given in FIG. 6. AA downregulates the viral oncoproteins E6 and E7 at 12 h, thus leading to the stabilization of p53 at 12 h and p21 at 24 h enabling cell cycle arrest at 24 h. The mitochondrial depolarization begins at 24 h along with other events like cleavage of caspase 8 and 3 and ending in apoptosis at 48 h. Caspase 9 activation precedes these events as it is already cleaved at 12 h. It could also be due to the down-regulation of cIAP2, which might occur as a response to the downregulation of viral oncoproteins. Thus, overall, our results provide new insights into the possible mechanisms of AA anticancer activity. These results also point to the prospective use of Anisomelic acid as a potent compound against cervical cancer and anti-HPV therapy.

Figure 7:
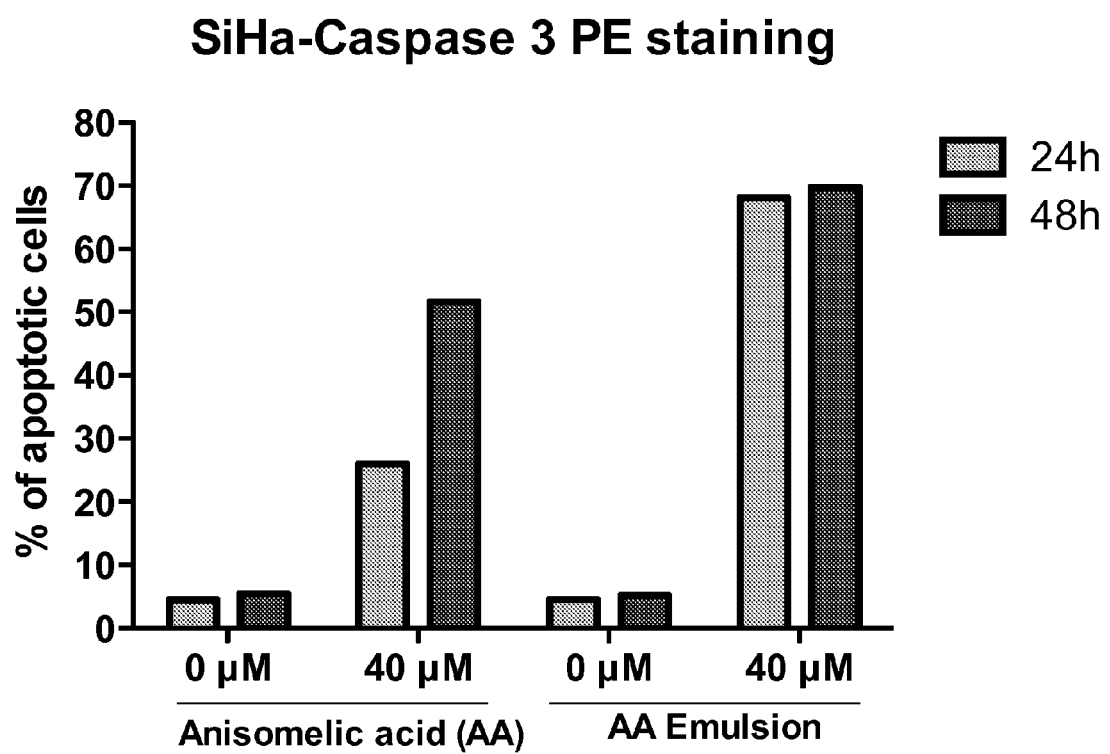
FIG. 7 shows the caspase-3 activation by AA and AA emulsion at 40 µM at 24 and 48 h.

We incubated the SiHa cells with 0 and 40 μM AA and AA emulsion as AA induced higher percentage of apoptosis at 40 μM for 24 and 48 hours, and determined the percentage of cells that contained activated caspase-3 as a measure of apoptosis. A marked activation of caspase-3 was observed at 24 h itself with AA emulsion compared with AA (FIG. 7).

CAM inoculated tumors were treated with emulsions with or without AA and the results reveal that AA suppresses the growth of SiHa tumor. The emulsion without AA is not toxic to the tumor itself (FIG. 8).

Summarizing the above results it can be noted that restoration of p53 or p21 function by blocking the activity of E6 and E7 serves as an interesting and important therapeutic target in these cancer cells. In the present invention, the effects of the natural diterpenoid anisomelic acid (AA) and salts thereof have been examined in a HPV-positive cervical cancer cell line (SiHa). Treatment with AA results in depletion of the E6 and E7 proteins. Consequently, p53 and the p53-responsive gene, p21, were dramatically induced, as evidenced by the above results, leading to G2/M-phase cell cycle arrest. AA-mediated cell cycle arrest and p21 expression were greatly reduced when p53 was down-regulated by p53-shRNA.

AA induces p53-independent apoptosis primarily by downregulation of the cellular inhibitor of apoptosis 2 (cIAP2) protein resulting in intrinsic activation of apoptotic caspases. Treatment of SiHa cells with AA emulsions exhibit higher apoptosis at 24 h itself and the AA emulsions are efficient in suppressing the tumors in CAM models. The present invention therefore provides for the use of AA in restoring p53-mediated growth arrest and inducing apoptosis in cervical carcinoma cells. It can, therefore, by itself or by using the its molecular principle, be used in developing therapies against cervical cancer. In addition, this principle can be employed in other HPV-mediated cancers, such as vulvar, vaginal, penile, anal, and some oropharyngeal cancers.

AA acts through a unique mechanism that enables specific targeting of HPV-positive cervical cancer cells. Our results show that the molecular principle of AA can be employed when developing drug molecules both for anti-cancer and for anti-HPV therapy.

Apart from cancers, genital warts are the most common disease manifestation of HPV and can lead to benign and neoplastic genital HPV associated diseases. Hence, these results point to the use of AA and derivatives thereof as a potent pharmacological strategy to develop therapies against cervical cancer, HPV mediated genital warts and prevention of HPV-mediated cancer risk. In addition, HPV is the most common cause of other types of warts, AA and the molecular principle of AA can also be employed in treatments against non-genital warts.

In the treatment of warts, Anisomelic acid and salts thereof can be administered topically. Anisomelic acid and salts thereof can be administered at dosages of 1 to 1000 mg on the surface of the treated object, i.e. for example on the wart infested skin. Use of Anisomelic acid and salts thereof in the form of an oil-in-water emulsion of the kind discussed above.

REFERENCES

Arisawa, M. et al., 1986. Biological active macrocyclic diterpenoids from Chinese drug "Fáng Féng Cáo"; II. Derivatives of ovatodiolids and their cytotoxity. *Planta medica*, (4), p. 297-9.
Marshall, J. A. & DeHoff, B. S., 1987. Cembranolide total synthesis. Anisomelic acid. *Tetrahedron*, 43(21), p. 4849-4860.
Marshall, J. A. & DeHoff, B. S., 1986. Stereoselective total synthesis of the cembranolide diterpene anisomelic acid. *Tetrahedron Letters*, 27(40), p. 4873-4876.
Tius, M. A, 1988. Synthesis of cembranes and cembranolides. *Chemical Reviews*, 88(5), p. 719-732.

The invention claimed is:

1. A pharmaceutical composition for use in anti-viral cancer treatment in mammals, comprising a therapeutically effective amount of an emulsion of Anisomelic acid or salts thereof.

2. The pharmaceutical composition according to claim 1, comprising Aniosomelic acid or salts thereof in the form of an aqueous, oleaginous suspension, dispersion, as a sterile powder capable of being used for extemporaneous preparation of injectable solutions or dispersions, or a solution or suspension in non-toxic diluent or solvent.

3. The pharmaceutical composition according to claim 1, wherein the Aniosomelic acid or salts thereof are provided in the form of a self-microemulsifying drug delivery composition.

4. The pharmaceutical composition according to claim 1, for treatment or prevention of cancer or a similar condition wherein the p53 pathway is deregulated by viral oncoproteins.

5. The pharmaceutical composition according to claim 1, for treatment or prevention of cervical cancer.

6. The pharmaceutical composition according to claim 1, for down-regulating oncoproteins and cellular inhibitor of apoptosis protein 2 (cIAP2).

7. The pharmaceutical composition according to claim 1, for reactivating the cell cycle arrest by activating p53-p21 pathway and also inducing p53-independent apoptosis.

8. The pharmaceutical composition according to claim 1, for use in treatment of Human Papilloma Virus mediated cancer.

9. A pharmaceutical composition comprising a therapeutically effective amount of an emulsion of Anisomelic acid or salts thereof, for use in treatment of conditions selected from the group consisting of benign or neoplastic genital Human Papilloma Virus associated diseases and non-genital warts.

10. A pharmaceutical composition comprising a therapeutically effective amount of Anisomelic acid or salt thereof in an oil-in-water emulsion or in a precursor thereof.

11. The pharmaceutical composition according to claim 10, comprising a therapeutically effective amount of Anisomelic acid or salt thereof in an isotropic mixture of at least one oil and at least one surfactant or, alternatively, in a hydrophilic solvent and a co-solvents or surfactant or a combination thereof.

12. The pharmaceutical composition according to claim 11 being capable of forming a fine oil-in-water (o/w) micro emulsion upon agitation followed by dilution in aqueous media.

13. The pharmaceutical composition according to claim 10, wherein it further comprises adjuvants or additives selected from the group of antioxidants, co-surfactants and co-solvents and combinations thereof.

14. The pharmaceutical composition according to claim 10, provided in the form of a soft or hard gelatin capsule filled with the emulsion.

15. A method of treating cancer or a similar condition in a mammal wherein the p53 pathway is deregulated by viral oncoproteins E6 and E7, comprising administering a therapeutically effective amount of an emulsion of Anisomelic acid or salts thereof to said mammal.

16. The method according to claim 15, comprising treating cervical cancer.

17. The method according to claim 15, comprising down-regulating oncoproteins and cellular inhibitor of apoptosis protein 2 (cIAP2).

18. The method according to claim 15, comprising reactivating the cell cycle arrest by activating p53-p21 pathway and also inducing p53-independent apoptosis.

19. The method according to claim 15, comprising treating Human Papilloma Virus mediated cancer.

20. The method according to claim 15, comprising administering a therapeutically effective amount of an emulsion of Anisomelic acid or salts thereof to a mammal in a dosage of 0.001 mg/kg to about 1,000 mg/kg body weight per day.

21. A method of treating benign or neoplastic genital Human Papilloma Virus associated diseases comprising administering a therapeutically effective amount of an emulsion of Anisomelic acid or salts thereof to a mammal in need thereof.

22. The method according to claim 21, comprising topically administering Anisomelic acid or salts thereof to the mammal.

* * * * *